US008477955B2

(12) United States Patent
Engle et al.

(10) Patent No.: US 8,477,955 B2
(45) Date of Patent: Jul. 2, 2013

(54) METHOD AND APPARATUS FOR CONTROLLING A HEADPHONE

(75) Inventors: Joseph Craig Engle, Carmel, IN (US); Gregg Michael Morgan, Carmel, IN (US); Francis Arthur Davenport, Haddonfield, NJ (US)

(73) Assignee: Thomson Licensing, Boulogne Billancourt (FR)

( * ) Notice: Subject to any disclaimer, the term of this patent is extended or adjusted under 35 U.S.C. 154(b) by 1504 days.

(21) Appl. No.: 11/663,114

(22) PCT Filed: Jul. 14, 2005

(86) PCT No.: PCT/US2005/025062

§ 371 (c)(1),
(2), (4) Date: Mar. 14, 2007

(87) PCT Pub. No.: WO2006/036262

PCT Pub. Date: Apr. 6, 2006

(65) Prior Publication Data

US 2009/0046868 A1 Feb. 19, 2009

Related U.S. Application Data

(60) Provisional application No. 60/612,626, filed on Sep. 23, 2004.

(51) Int. Cl.
*A61F 11/06* (2006.01)

(52) U.S. Cl.
USPC ............ 381/71.1; 381/74; 379/430

(58) Field of Classification Search
USPC ............ 381/74, 56, 57, 110, 107, 370, 309, 381/1, 17, 95, 92, 71.1, 71.6–71.8, 311, 96, 381/71.13, 94.1–94.5, 58, 72; 379/430; 704/274; 446/175
See application file for complete search history.

(56) References Cited

U.S. PATENT DOCUMENTS

| | | | | |
|---|---|---|---|---|
| 4,185,168 | A | 1/1980 | Graupe et al. | |
| 5,706,399 | A * | 1/1998 | Bareis | 704/274 |
| 6,078,672 | A | 6/2000 | Saunders et al. | |
| 6,160,893 | A | 12/2000 | Saunders et al. | |
| 6,445,799 | B1 | 9/2002 | Taenzer et al. | |
| 6,814,643 | B1 * | 11/2004 | Dooley et al. | 446/175 |
| 7,065,219 | B1 * | 6/2006 | Abe et al. | 381/74 |
| 2001/0046304 | A1 * | 11/2001 | Rast | 381/74 |
| 2002/0039424 | A1 | 4/2002 | Watanuki | |
| 2004/0179694 | A1 * | 9/2004 | Alley | 381/55 |
| 2005/0254665 | A1 | 11/2005 | Vaudrey et al. | |

FOREIGN PATENT DOCUMENTS

| | | |
|---|---|---|
| EP | 0390386 | 10/1990 |
| FR | 2761260 | 10/1998 |
| JP | 6-3344457 | 2/1994 |
| WO | WO 93/26085 | 12/1993 |
| WO | WO00/10362 | 2/2000 |

OTHER PUBLICATIONS

Search Dated Jan. 20, 2006.
Search Dated Mar. 1, 2006.

* cited by examiner

*Primary Examiner* — Lun-See Lao
(74) *Attorney, Agent, or Firm* — Robert D. Shedd; Reitseng Lin

(57) ABSTRACT

A method for controlling a headphone having a microphone for receiving noise and user signals, the received noise being used to reduce noise at an output of the headphone, includes detecting a signal by the microphone; if the signal has a predefined characteristic, the signal is mapped to a control command; and the headphone is operated according to the command.

19 Claims, 5 Drawing Sheets

METHOD AND APPARATUS FOR CONTROLLING A HEADPHONE

This application claims the benefit, under 35 U.S.C. §365 of International Application PCT/US2005/025062, filed Jul. 14, 2005, which was published in accordance with PCT Article 21(2) on Apr. 6, 2006 in English and which claims the benefit of U.S. provisional patent application No. 60/612,626, filed Sep. 23, 2004.

FIELD OF THE INVENTION

The present invention relates to headphones, and particularly to active noise cancellation in headphones.

BACKGROUND OF THE INVENTION

Many headphones having one or two headphones, particularly those that provide noise cancellation, generally include a cable mounted with an "in line" control pod. Such pods are necessarily small in size and weight, and, consequently, provide diminutive controls, levers, and switches for controlling operation of the headphones. These control elements may be so small that they provide poor visual and tactile feedback of the adjustment.

If control elements are mounted on the headphones, the operation of the headphones becomes even more difficult because the control elements are not visible and the operation may interfere with hairstyling, glasses, and ears. A user generally has to repeatedly take the headset on and off to adjust the controls.

In addition to the problem of using the controls, the control elements may add weight to a headphone, making a user wearing the headphone more uncomfortable. Adding controls to a headphone may have other undesirable effects. It may increase the size and cost of a headphone. At the same time, it may decrease the reliability of the headphone because these controls are generally small in size, making them less durable. As more controls are added to the design in the form of additional switches or knobs, the more complex the unit becomes, thereby decreasing the overall usability of the headphones. Users may be intimidated by the large number of controls. Furthermore, labeling the controls becomes an issue as well. As the space is limited, label space is also limited. As such, there is a need to reduce the number of input mechanisms for controlling a headphone, while supporting more control functions.

Another problem of a conventional noise reduction headphone is that fixed noise reduction filters are used, which limits the amount of noise reduction available, and does not allow a user to vary the noise canceling characteristics based on the external noise. For example, a user may wish that certain types of noise, such as voices or emergency sirens, not be canceled. The types of noise that should be canceled, and those that should not be canceled, may vary depending on the environment where the headphones are worn. Accordingly, filters that meet these needs would be desirable.

SUMMARY OF THE INVENTION

The present invention overcomes the problems mentioned above by providing a headphone that allows the user to enter commands for operating the headphone using a microphone included with headphone. Headphone that provide noise cancellation generally include a microphone for sensing ambient noise. The present invention enables a user to enter commands via the microphone for controlling the operation of the headphone.

According to an aspect, the invention provides a method comprising the steps of: detecting a signal via a microphone; determining a characteristic of the detected signal; and controlling the headphone in accordance with the characteristic of the detected signal. The characteristic may include, for example, but not limited to, audio signals generated by the user tapping the headphones a specified number of times, a specified number of times with intervals that exceed a threshold length, and a specified number of times on a front microphone and a back microphone. The audio signal produced by a user tapping on the microphone, or a microphone dedicated to receiving user input, will have a definite frequency output and may be used by the system to recognize the user input.

According to another aspect, the invention provides a headphone, comprising: a microphone for receiving noise; a controller coupled to the microphone, wherein, in response to detection of a signal having a specified characteristic, the controller controls operation of the headphone in response to detection of the specified characteristic.

According to another aspect, the invention provides a microphone for a headphone, comprising: an input positioned in a recess below a surface of the headphone; a plate adjacent the input; a striking member having proximal and distal ends, the striking member situated in a first position in the absence of an applied force in which the proximal end is positioned to be engaged by a finger of a user, the striking member mounted so that the distal end strikes the plate when the striking member is urged toward the plate.

DETAILED DESCRIPTION

Figure 1:
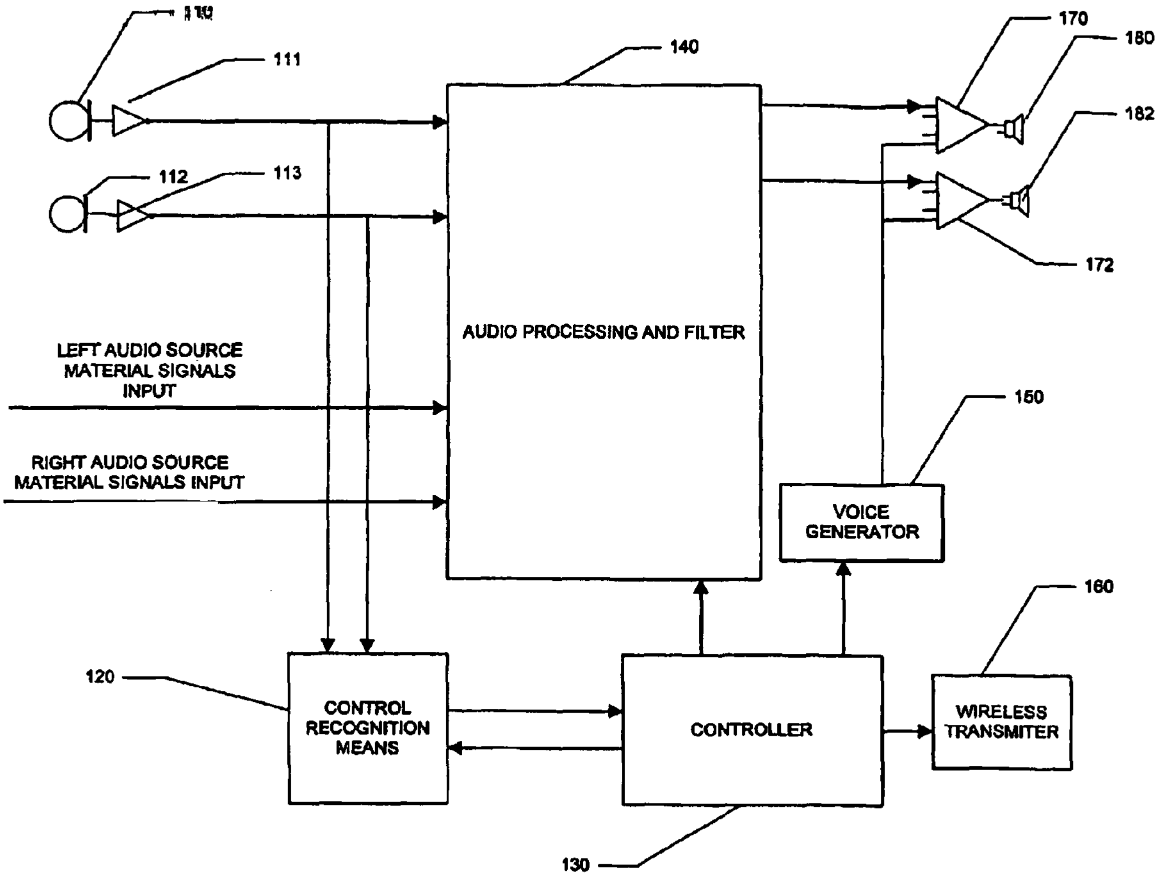
FIG. 1 is a block diagram of a headphone system in accordance with an embodiment of the invention.

FIG. 1 is a block diagram illustrating a headphone system according to an embodiment of the invention. Left noise sensing microphone 110 and right noise sensing microphone 112 detect signals, and in particular provide analog ambient noise signals to amplifiers 111, 113, respectively. The amplified ambient noise signals are provided to control recognition means (CRM) 120. CRM 120 determines if the noise signals have a specific, or particular, characteristic to determine if a user input signal is received. CRM 120 detects a user input signal, generated in response to user action, maps the user signal to a command, and sends the command to a controller 130. Controller 130 decodes the command and causes the headphone to operate in accordance with the command. The operation of the headphone may include changing a characteristic of sound output by the headphone. The characteristic may include volume, treble, bass, and/or selection or feature of active noise reduction filters.

Controller 130 instructs an audio processor and filter 140 to perform a function specified by the command. For example, if the command is to select a particular filter, the controller 130 instructs the audio processing and filter 140 to select that particular filter. If the command is to change the volume, the controller 130 instructs the audio processing and filter 140 to change the volume in accordance with the command.

The controller 130 can also provide a feedback to a user sending the command indicating that a command has been received or prompt a further command from the user. For example, the controller 130 may generate a beep, series of beeps, modulated tone, or synthesized voice into the headphones, indicating that a valid command has been received. In FIG. 1, a voice generator 150 (synthesizer) is included in the headset and the controller 130, through the voice generator 150, can speak to the user via a human voice with a message that indicates what command has been received. For example, the message of "Volume Up" indicates that the controller 130 has received a command to raise the volume.

Audio processing and filter 140 combines, in each channel, the audio source material signals and the ambient noise signals (which may be filtered), and outputs those signals to buffer amplifiers 170, 172. Signals from voice generator 150 are also coupled to buffer amplifiers 170, 172. Buffer amplifiers sum and amplify the received signals to provide driving signals to respective left and right speakers 180, 182.

Figure 2:
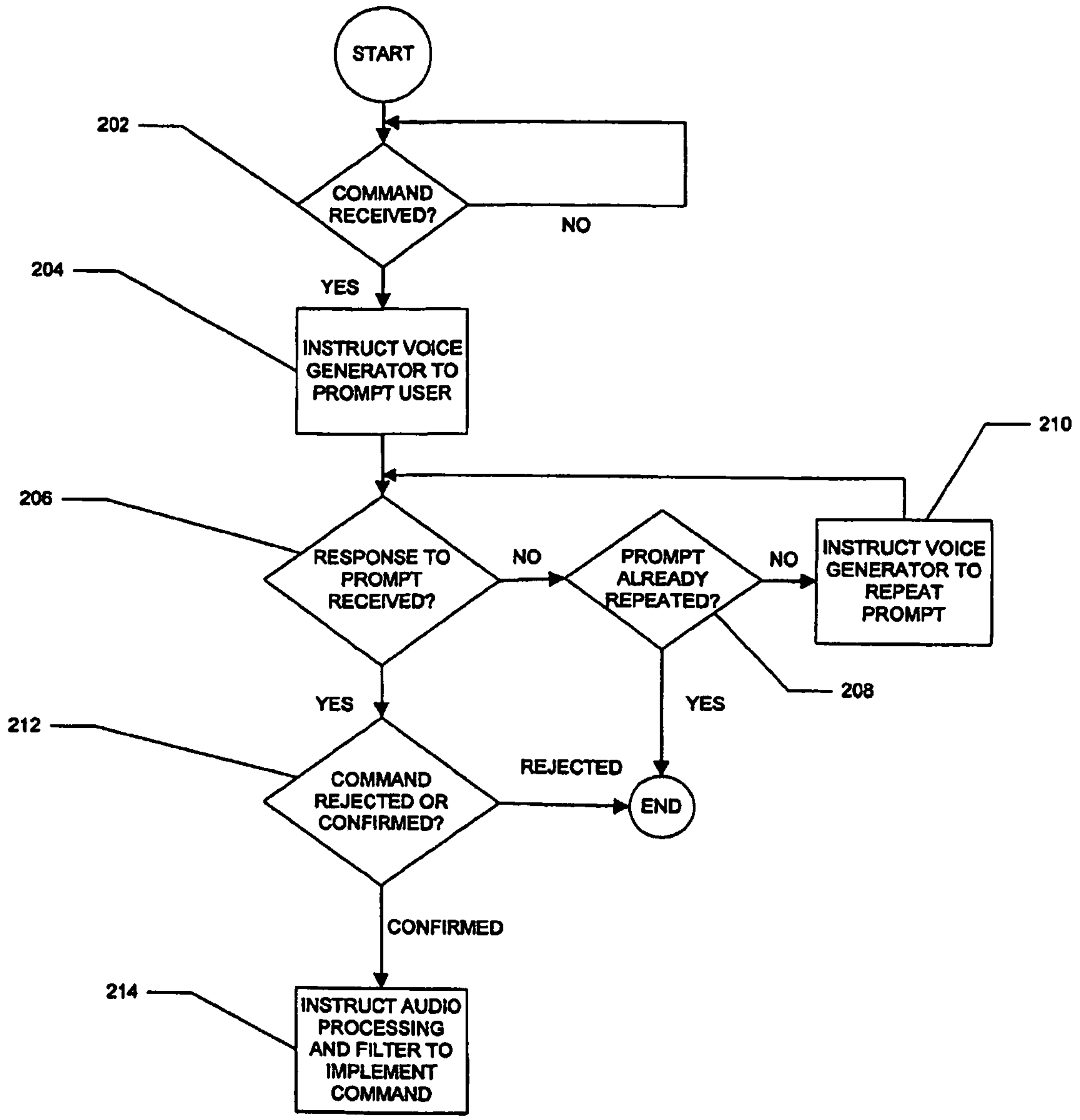
FIG. 2 is a process flow chart of a process for recognizing commands and providing commands in a system in accordance with an embodiment of the invention.

The controller 130 can provide a feedback by prompting a user to confirm whether the user has entered a particular command. For example, referring to FIG. 2, controller 130 may be checking for commands. If a command is detected, as indicated by 202 and 204, controller 130 instructs voice generator to prompt the user to confirm the command. For example, if the command is a command to increase the volume, the controller may cause voice generator 150 to generate the question "Volume Up?" to the user.

The user can send a signal, for example, tapping the microphone once to indicate a "YES" or send another signal, for example, tapping the microphone twice to indicate a "NO." The voice generator 150 may generate a prompt message such as "Tap once to confirm, tap twice to cancel." If no discernable response is received within a selected time period after the prompt, the controller 130 may repeat the prompt once, as indicated at 206, 208 and 210, or simply disregard the command. If the command is rejected by the user, such as by inputting a "NO", in response to the prompt, then the process is at an end, as indicated at 212. If the command is confirmed, such as by a "YES" received in response to the prompt, as indicated at 214, then controller 130 instructs audio processing and filters 140 to execute the command, such as increasing the volume.

The headset may be configured to transmit control signals to other apparatus remote from a headset user, such as a telephone, CD player, DVD, VCR, television, MP3 player, karaoke machine, and home security system. The step of operating the headphone, in response to the command, may thus include transmitting control signals. Control signals can be wirelessly sent from a wireless transmitter 160, which may operate employing an infrared, ultraviolet, radiofrequency, or other carrier, with suitable modulation. Wireless transmitter 160 may also be configured for reception of signals. For example, the remote apparatus may be configured to provide an acknowledgment signal to the headset, and the wireless transmitter may receive this signal and transmit the signal to the controller. Wired transmission to remote devices may also be employed.

Illustratively, several methods of inputting a command are possible, each creating a condition in the system that is not normally present. This condition can be used to trigger the controller 130 to indicate that an incoming command is being received.

In the first example, a user can create a signal having a predefined, or specified, characteristic using a finger to strike, tap, or touch a headphone on or near one of the microphones, one or more times in succession. The striking, tapping or touching of the headphone on or near one of the microphones creates a high-amplitude, short duration sound signal. The terms "tap" and "tapping" are used herein to designate the creation of such a high-amplitude, short duration sound pulse by striking, tapping, touching or otherwise contacting any portion of a headset on or near a microphone input, as well as the pulses themselves. One predefined characteristic of a signal may be the combination of high-amplitude and short duration. Other predefined characteristics may be the numbers of pulses received in an time interval, the duration of time intervals between such pulses, and the patterns of pulses provided at various microphones on headphones having more than one microphone. The control recognition means (CRM) 120 can decode this signal by looking for presence of the high amplitude pulses, with the command being determined by the timing and/or number of pulses received. As an example of the timing, a first tap followed by a second tap within a threshold time interval may have a different meaning than a first tap followed by a second tap after a time interval greater than the threshold.

Since two or more microphone inputs may exist in a headset, the variety of commands may be increased by providing different meanings to the same pattern of taps on different microphones, and as such, a number of different commands are possible. The CRM recognition abilities can be further improved by tapping or touching both microphone inputs to signal the CRM. For example, in a headphone having right and left microphone inputs, tapping on or near the right microphone input twice, then on or near the left microphone twice, might signal to the controller to increase the filter bandwidth, whereas tapping twice on or near the left microphone input first, then tapping twice on or near the right microphone input, might mean to decrease the filter bandwidth.

Additional microphones may be provided on the headset, suitably spaced from one another to reduce the possibility of the user inadvertently activating a microphone other than that intended. For example, microphones may be provided on the front and rear of a headphone on each side. This may permit the user to obtain the benefit of relatively complex commands afforded by multiple microphones, without the need to use both hands to provide inputs.

Table 1 shows an exemplary mapping between input tapping signals and commands.

TABLE 1

| USER STIMULUS | HEADPHONE RESPONSE |
|---|---|
| Double tap right microphone | Volume up |
| Double tap left microphone | Volume down |
| Triple tap right microphone, followed by single taps of the left microphone. | Following the triple tap of the right microphone, each tap of the left microphone switches filters, cycling through all of them. If no tap occurs in the left microphone for 5 seconds, the cycling stops (function times out). |
| Double tap right microphone, followed by a single tap on the right microphone. | Headphones turn off. |
| Four taps on the right microphone put the headphone in a | The four taps bring up a menu on a remotely controlled device. This device |

TABLE 1-continued

| USER STIMULUS | HEADPHONE RESPONSE |
|---|---|
| remote control mode, where the RF or IR or other link to another device is used to control the other device. Now a right tap means move the cursor right, and a left tap means move cursor down. A double tap in either side means select the option. | has a menu system that responds to commands sent from the headphone. |

Another method of providing commands using headphone microphone inputs is to cover one of the microphone inputs, such as with a finger. In a headphone with two inputs, the CRM may be configured to compare noise levels received at the two inputs, and only to accept control signals if the comparison indicates a threshold difference between the respective noise levels. This condition may only be operative if the higher detected ambient noise level is above a threshold, as covering one of the microphones will result in a relatively small difference in environments with very low ambient noise levels. The CRM then actively compares the received ambient noise on the higher noise channel with known patterns.

As with tapping a microphone, the number of possible commands is increased since there are two microphone in the system. For example, covering the left microphone and tapping twice on the right microphone might signal to the controller to increase the headset volume, whereas covering the right microphone and tapping twice on the left microphone might mean to decrease the volume.

Of course, other methods of providing commands using the microphone inputs on a headphone can be used as well. For example, quiet periods may be created by covering a microphone input. The CRM can detect the duration of a quiet period, the interval between two quiet periods, or the combination of both for each or both headphones, and map an input signal to a particular command.

The system and method described above obtains at least the following advantages over conventional designs that utilize external headphone controls. First, commands may be provided even in a high noise environment. Second, in some embodiments, no moving parts, such as mechanical switches or knobs, are needed, thereby increasing reliability and decreasing costs of fabrication. Third, no external headphone controls are needed, so no weight is added to the design, and no space is used on the headphone. Fourth, the user does not need to remove the headphones in order to change settings. Fifth, no openings in a headphone housing are needed to accommodate switches and knobs, the headphones remain better sealed against the environment. Sixth, less space is required for labels.

As an alternative or in addition to the techniques above, the CRM and controller (or an additional signal processor) may perform voice recognition. Recognized voice commands will result in prompts and/or commands issued to audio processing and filters as described above. Since the spectral characteristics of a voice message are quite different from that of a noise signal, the CRM may periodically sample signals received from the microphones, and, if the spectral characteristics match, pass the received signal to the controller or a DSP for voice recognition. If the CRM has sufficient processing capability, the CRM may perform voice recognition functions. The controller may translate the received voice message into a particular command, and either prompt the user or instruct a change in settings, as appropriate.

Figure 3:
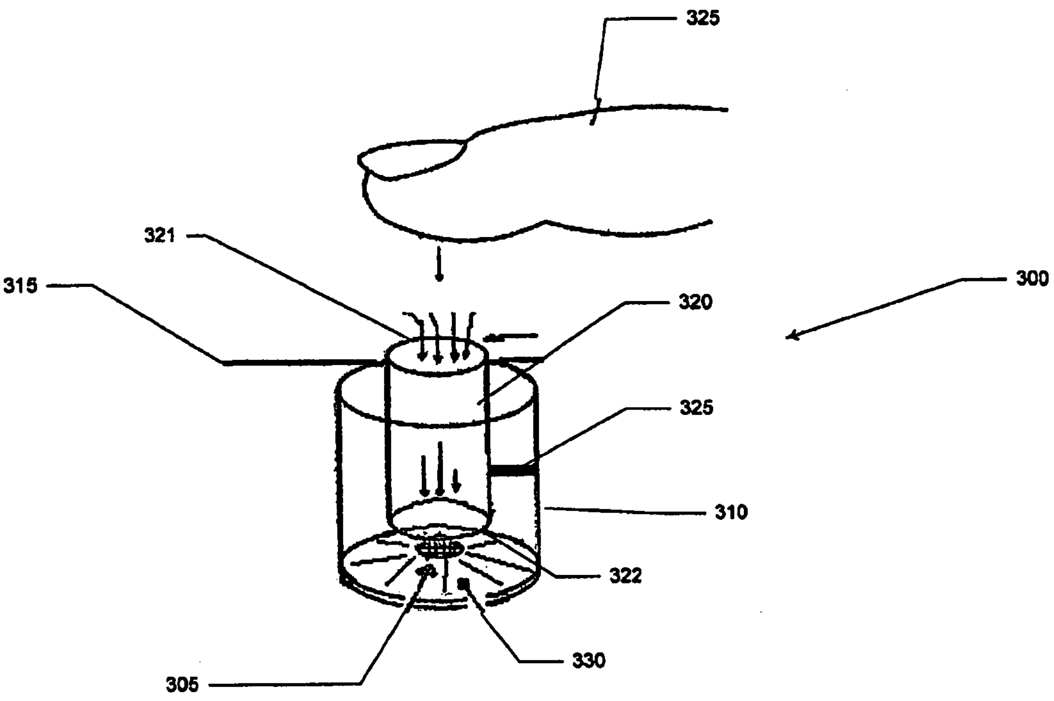
FIG. 3 is an illustration of a microphone device for receiving a signal in an embodiment of the invention.

Referring now to FIG. 3, to enhance the detectability of an input tapping signal, a microphone structure 300 may be provided in which a microphone input 305 is positioned in a bore or recess 310 below the generally smooth surface 315 of the headphone. A striking member 320 is mounted in a spring-loaded manner, such as by fixing to one end of flexible retaining arm 325, which is fixed at its opposite end to an inner surface of recess 310. When the striking member is in a first position, and no force is exerted, the proximal end 321 of striking member 320 is positioned to be engaged by a finger of a user. Proximal end 321 of striking member 320 may extend above the surface 315 when striking member 320 is in a first position. However, depending on such factors as the diameter of the opening of bore 310, proximal end 321 of striking member 320 may be sufficiently accessible to a finger to lie flush with or recessed slightly below surface 315. In the illustrated embodiment, striking member 320 is in the form of a hollow cylinder having a continuous side wall.

Striking member 320 may take other forms, such as a rod of narrow diameter relative to the diameter of bore 315, so that striking member 320 interferes as little as possible with transmission of sound to microphone 310. A strike plate 330, which may be of any suitable shape, is located near microphone 320. Strike plate 330 is preferably shaped suitably to provide a target for distal or striking end 322 of striking member 320. In the illustrated embodiment, striking member 320 is a hollow right circular cylinder, open at both ends, and strike plate 330 is a planar, circular member, so that the entire distal end of striking member 320 contacts strike plate 330. Both the distal end 322 of striking member 320 and strike plate 330 are preferably rigid materials, so that an impact of distal end 322 on strike plate 330 produces a short duration, high-intensity pulse. This pulse sound is consistent and hence may be easier to distinguish from ambient noise than the sound of a finger striking the surface of a headphone.

When no command is being provided to the microphone, ambient noise travels both through, as indicated by the arrows in FIG. 3, and around the cylindrical striking member 320 to the microphone input 305. When the user desires to provide a command by tapping, the user's finger pushes down on the cylindrical striking member 320, which then moves toward the microphone and strikes the strike plate 330 around the microphone, thereby producing a short duration, high amplitude tap sound. The user's finger closes the proximal opening of the cylindrical striking member 320, thereby reducing the ambient noise reaching the microphone prior to and after the tap sound. This arrangement renders the discrimination of the tap sound easier, as the contrast between the tap sound and the reduced ambient noise level is more pronounced than the contrast between the general ambient noise level and the tap sound.

Figure 4:
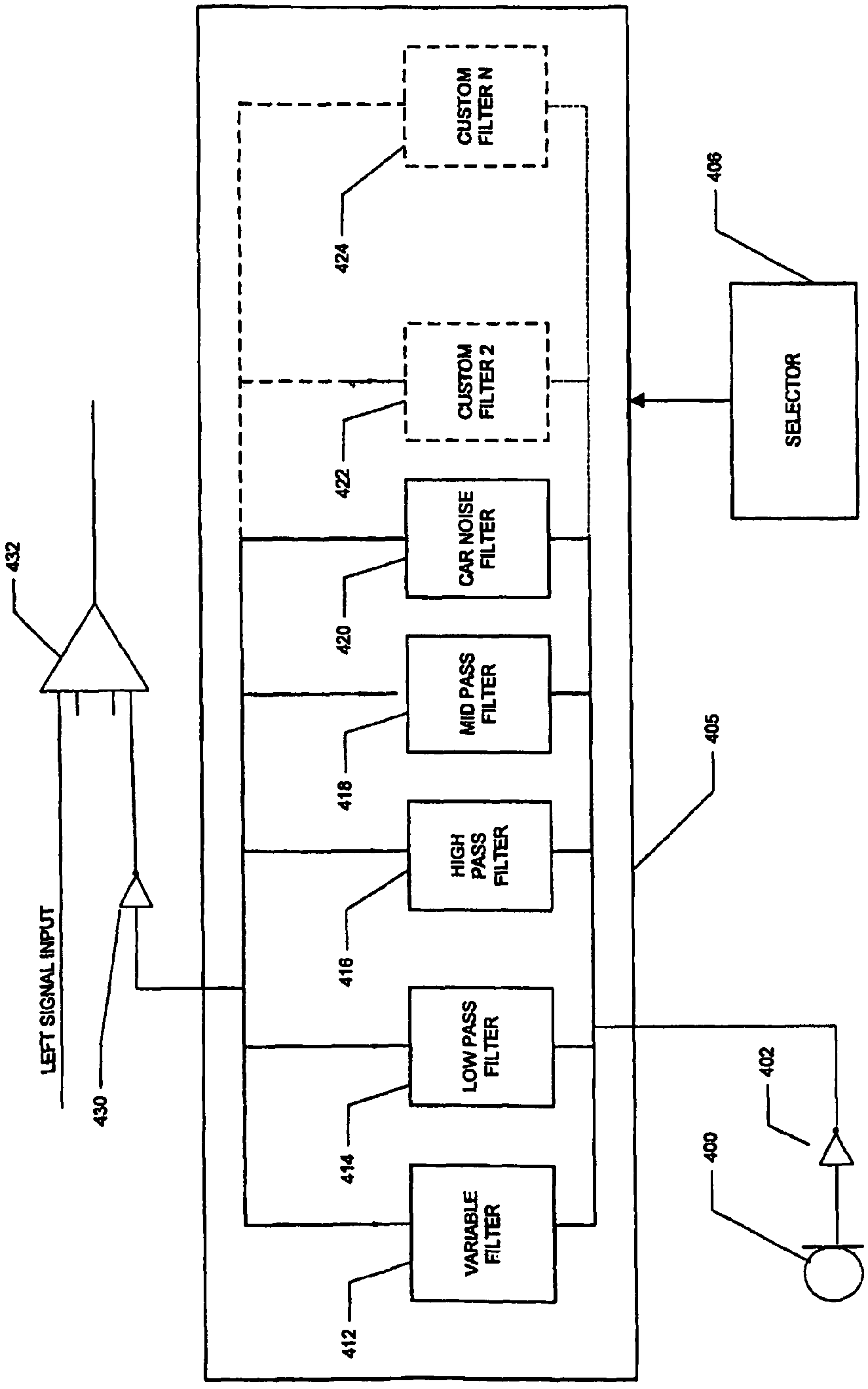
FIG. 4 is a block diagram of a portion of a headphone system having a plurality of filters in accordance with an embodiment of the invention.

In another embodiment of the invention, a headphone is provided with active noise reduction including active noise reduction filters applicable to one or more predefined frequency bands selectable by a user, and filters with frequency bands and/or gains selectable by a user, as illustrated in FIG. 4.

Referring to FIG. 4, ambient noise from a microphone 400 is buffered and amplified by a buffer amplifier 402. The output from the buffer amplifier is fed to one of the filters in filter block 405, as selected by the user employing selector 406. Selector 406 may operate as set forth above in connection with FIGS. 1 and 2. The particular filter may be selected by commands provided to the microphones, in one of the manners described above, or by a switch of a different type. The output signal from a selected filter is inverted and amplified by an inverting amplifier 430. The output of the inverted noise signal is added to an input audio signal by a summing amplifier 432 and the sum signal is then fed to a speaker (not shown) in the headphone, so that the output signal from the speaker can cancel or reduce the ambient noise present at an output of the headphone.

Switchable frequency bands, and high pass, low pass, and mid pass filters, as shown in FIG. 4, could be independently switched in. Two or more such bands may be activated at the same time. Variable filter 412 may include variable frequency, variable gain, and variable bandwidth, each of which parameters may be user-defined. These features permit a user great flexibility to cancel out a specific band of noise that is a problem. Low pass filter 414, high pass filter 416, and mid pass filter 418 may be individually tunable through a suitable user interface to permit users to select ranges of frequencies for active noise cancellation. Car filter 420, and custom filter 2 through custom filter N, including as many custom filters as may be desired, may be provided. These custom filters may be specially tuned filters for an environment in general terms, such as the interior of a passenger car. Custom filters may be provided for specific variations on such an environment, such as specific makes and models of automobile, noise generated by various road surfaces, and such variables as open and closed windows, air conditioner noise, and/or fan noise. The custom filters can be specially tuned filters for other environments, such as the cabin of a jet airplane, similarly configured passenger cabins of propeller planes, helicopter environment and associated noise, noises of motors found in a home, office or other building, such as air conditioner noise (e.g., window unit), vacuum cleaner, and industrial environments, such as warehouses and factory environments.

Figure 5:
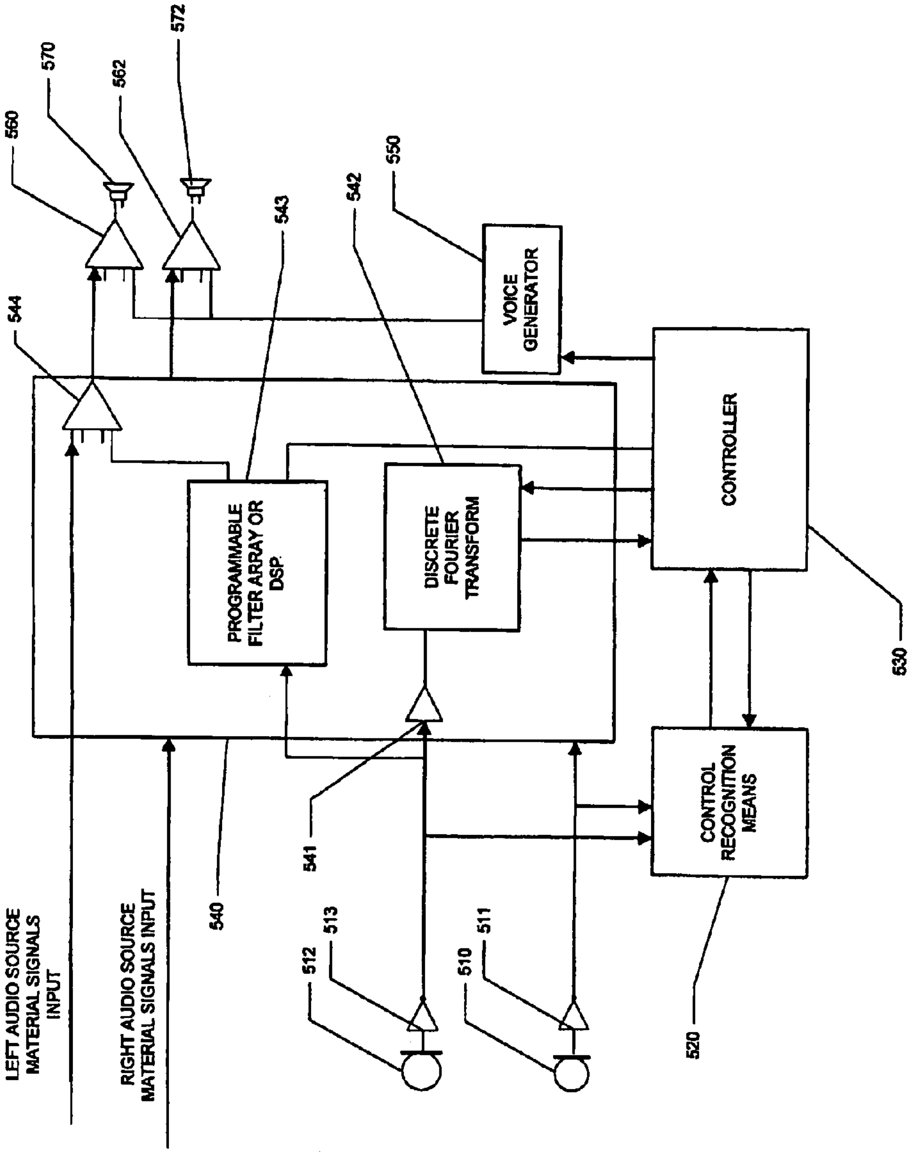
FIG. 5 is a block diagram of a headphone system configured for digital signal processing in accordance with an embodiment of the invention.

FIG. 5 illustrates another embodiment of the invention, where a digital signal processing (DSP) system is added to characterize the received noise, for example using spectral and amplitude information obtained through a spectral analysis, and program a programmable filter array or a digital signal processor according to the characterization. In this way, noise cancellation or reduction can be dynamically optimized during transient conditions, such as passing vehicles, trees, trains, or aircraft.

The noise processing of the left and right headphone is similar. For simplicity, FIG. 5 shows only the processing of the left headphone. Ambient noise is received at left and right noise sensing microphones 510, 512, which are amplified by amplifiers 511, 512. The received ambient noise signals are provided to control recognition means 520, similar to control recognition means 120 discussed above. The received ambient noise signals are provided to audio processing and filters 540, and are converted into digital signal by an analog-to-digital converter 541. The digitized noise signal is discrete Fourier transformed at block 542 to obtain the spectra and amplitudes of the ambient noise. The spectrum and amplitude information is sent to the controller 530, which stores information in a memory on those bands in the ambient noise that should not be cancelled. For example, bands corresponding to human speech and emergency sirens should not be cancelled. Based on the received spectrum and amplitude information and the information in the memory, the controller 530 determines one or more bands of ambient noise to be cancelled or reduced, and instructs, the programmable filter array or DSP system 543 to construct filters to provide active noise cancellation for those bands that should be cancelled or reduced. The DSP system 543 performing the construction of the filter may be a programmable filter array or a digital signal processor. DSP system 543 may also invert the filtered passed signal and output the inverted signal to a summing amplifier 544.

Another input of summing amplifier 544 is coupled to left audio source materials input. Summing amplifier 544 sums the two received signals and the sum signal is digital to analog converted and input to one of buffer amplifiers 560, 562. Buffer amplifiers 560, 562, also receive signals from voice generator 550, which is similar to voice generator 150 of FIG. 1. Buffer amplifiers 560, 562 sum the received signals and provide an amplified output signal used to drive speakers 570, 572.

As an example of constructing the filters, assume that the controller decides that first and second frequency bands of the ambient noise should be cancelled or reduced, the controller instructs a digital signal processor included in the DSP system to construct two band pass filters for passing the respective first and second bands. These two band pass filters should be arranged in parallel, so that both bands are present at the output.

If a programmable filter array is used, the programmable array should includes many filters, each having a different passing band, and capable of being connected in parallel or in series in any combination.

If a digital signal processor is used to construct the filters, the digital signal processor should also perform the DFT as discussed above. In this embodiment, the ambient noise received by the microphone is converted to a digital signal by a second analog to digital converter, the digital signal is transformed into frequency domain, the digital signal in frequency domain is passed through the constructed filters, the filtered signal is inversely transformed into time domain, the filtered signal in time domain is inverted by an inverter, the inverted signal is converted to analog signal by a digital to analog converter, and the converted analog signal is then sent to the summing amplifier. The second analog to digital converter and the digital to analog converter are not shown for simplicity. The filters constructed by the digital signal processor can be IIR or FIR filters as known in the art.

If a digital programmable filter array is used, the received ambient noise is converted into digital, transformed into time domain, and the filtered signal is inversely transformed to time domain, inverted, and converted in a analog signal, as described above for using a digital signal processor.

If an analog programmable filter array is used, no analog to digital converter, digital to analog converter, and transformation is needed.

According to another aspect of the invention, after characterizing the noise, the controller based on the spectrum and amplitude information of the ambient noise selects one of the predefined filters as shown in FIG. 4 that is best able to cancel or reduce the type of the input noise.

The system preferably is automatic. However, the system may be started after receiving a particular user command. In addition, the system after deciding a filter or a set of filters in response to a user command can stop the processing, so that the determined filter arrangement is used until another user command for adjusting the filter arrangement has been received.

In one embodiment of the invention, a function and associated user command may be provided to have the system construct a filter to cancel noise received at a user-selected time. A function and associated user command may also be provided to have the system designate a certain frequency range as not to be cancelled, based on characterizing a sound received at a user-selected time. For construction, a user command is provided for construction of a filter. This command may be provided in any suitable manner, including through a special-purpose button, a pattern of controls, and/or a pattern of tapping. Upon receipt of the command, the system characterizes the sound received at the microphones. A filter is constructed to provide cancellation of sound within a frequency range determined by the received sound, such as a frequency range in which the received sound is above a threshold level. The constructed filter characteristics are stored in memory. The memory location is then associated with a user-defined command. For example, through voice prompts, the user may be able to select a name or set of commands for the memory location corresponding to the constructed filter.

In one example, a user might desire to optimize the system for driving in a car, and want to cancel road noise, but not voices. The user, while driving, with little sound other than road noise being received, would provide the appropriate command to the system by pressing an exemplary "CANCEL NOISE" button. In response to the command, the DSP would analyze the received acoustic signal, which, as noted, at least a majority of which is in the form of road noise. The DSP may determine that the noise associated with the acoustic signal is in a frequency band from 50 Hz to 400 Hz. The system then constructs a filter that operates to effectively cancel the noise corresponding to this frequency band associated with the received signal. Now the system stores the constructed filter, in the form of parameters defining the determined frequency band, in memory. The user may be provided a command that causes the constructed filter to be activated, thereby causing the system to cancel incoming microphone signals in this frequency band.

For selection of a frequency band to be passed through (i.e., frequency components of a received signal that are not intended to be subject to noise cancellation filtering), a user command is provided for designation of a band to be passed through. This command may be provided in any suitable manner, including through a special-purpose button, a pattern of controls, and/or a pattern of tapping. Upon receipt of the command, the system characterizes the sound received at the microphones. A pass-through band, defined by a frequency range determined by the received sound, such as a frequency range in which the received sound is above a threshold level, may be stored in memory. The user may be provided with an option to have received sound in this pass-through band always pass through, or pass through only when the user so selects. If this pass-through band is only to be passed through upon user selection, the memory location is then associated with a user-defined command. For example, through voice prompts, the user may be able to select a name or set of commands for the memory location corresponding to this pass-through band.

By way of example, a user might want to be able to hear an individual talking. The user may, while the individual is talking, and relatively little other sound is being received, communicate the command to create a pass-through band, such as through an exemplary "PASS THROUGH" button. In response to the command, the system would analyze the received sound, and determine that the sound is above a threshold level in a band, such as a band from 500 Hz to 1300 Hz. Now the system would store the pass-through band, in the form of parameters defining this frequency band, in memory. If desired, the system may then pass through all incoming microphone signals in this pass-through band. Alternatively, the user may be prompted to designate a command to selectively activate the pass through function for sounds in this pass-through band.

Pass-through bands may be predetermined as a default or as a feature that cannot be changed by the user. For example, a band corresponding to an emergency siren, such as 900 Hz to 1000 Hz, could be predetermined as a pass-through band. Such a pass-through band could be automatically activated when a particular custom filter, such as a car noise custom filter, is selected by the user. Alternatively, a command may be provided for the user to selectively activate pass through of such a band.

A pass-through band may, as a default, always override cancellation of frequencies in the pass-through band by an existing or constructed filter. Alternatively, the user may have the option of having a pass-through band override one or more cancellation filters. For example, if, in the example above relating to road noise, the constructed filter canceled received sound in the range from 50 Hz to 400 Hz, but the pass-through band created by receiving the individual's voice was from 300 Hz to 1300 Hz, the default could always select the overlap, in the 300 Hz to 400 Hz range, to be passed through. Alternatively, the default could always select the overlap to be canceled. In either case, the user may have the option of overriding the default.

The system can be implemented using discrete elements, or done entirely in a digital signal processor. That is the analog-to-digital conversion and discrete Fourier transform (DFT) calculation, applied filter, and summing function can all be performed in a DSP integrated circuit (IC). Additionally, any of these functions could be performed by the controller if the controller has the capabilities. That is, if the controller has an A/D input and has the processing power, and a digital-to-analog conversion (d/a) output, this could all be done by the controller.

An advantage of this invention is that the headphone may be controlled in response to user input, without adding control elements that require the addition of user adjustable elements to the headphone or a control pod associated with the headphone. A further advantage of this invention is that the programmable filters and the ability to characterize the noise, allow any noise spectra to be dynamically cancelled or reduced. This aspect of invention can be implemented completely by software or in one IC, and is operative with any noise environment. A major advantage of using programmable filters is that one could exclude filtering of signals in certain frequency bands or amplitudes, such as human speech and sirens, for safety, legal, or other reasons.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

The invention claimed is:

1. A method for controlling a headphone, comprising the steps of:

receiving a noise signal via a microphone;

detecting the noise signal;

determining a characteristic of the detected signal; and controlling operation of the headphone in accordance with the characteristic of the detected noise signal it the characteristic indicates that the detected noise signal includes a user generated signal exhibiting said characteristic, wherein the controlling step further comprises selecting a particular noise cancellation function in response to the characteristic of the user generated signal, wherein the particular noise cancellation function is directed to cancellation of a signal other than the user generated signal.

2. The method of claim 1, wherein the microphone is disposed on the headphone and the user generated signal is created by a user touch of the headphone on or near the microphone.

3. The method of claim 1, further comprising the step of generating one of a confirmation message and a further prompting message in response to determining step if that characteristic indicates that the detected noise signal includes the user generated signal.

4. The method of claim 1, wherein the controlling step comprises changing an operating characteristic of a selected noise cancellation function in response to the characteristic of the generated signal.

5. The method of claim 1, wherein the controlling step comprises constructing a noise cancellation function to cancel noise received at a user selected time.

6. The method of claim 5, wherein the constructed noise cancellation function is stored in memory, and further comprising activating the constructed noise cancellation function in response to a user generated signal.

7. The method of claim 6, further comprising, in response to a user generated signal, selecting noise received at a user-selected time in a band to be in a pass-through band, whereby the selected noise within the pass through band is not cancelled.

8. The method of claim 1, wherein the signal is detected by a microphone, and the characteristic of the detected noise signal is a predetermined pattern of pulses received at the microphone.

9. The method of claim 1, wherein the detected noise signal comprises pulses and intervals therebetween, wherein intervals between pulses exceeds a threshold.

10. A headphone, comprising:

a microphone for receiving noise;

a detector for determining a presence of a characteristic in the noise indicative of a user generated noise signal;

a controller, responsive to detection of said characteristic, for controlling operation of the headphone in response to the user generated signal, and said controller also for selecting a particular noise cancellation function according to the user generated signal, wherein the particular noise cancellation function is directed to cancellation of a signal other than the user generated signal.

11. The headphone of claim 10, further comprising a plurality of filters, the filters being selectively used by the controller for providing noise cancellation.

12. The headphone of claim 11, wherein the controller generates one of a confirmation message and a further prompting message in response to determining that the detected signal has the characteristic and controlling the operation of the headphone in response to a further user generated signal input.

13. The headphone of claim 11, wherein the controller selects one of a plurality of filters for providing noise cancellation in response to the user generated signal having the characteristic.

14. The headphone of claim 11, wherein the controller selects an operating characteristic of a selected filter for providing noise cancellation in response to the user generated signal having the characteristic.

15. The headphone of claim 11, wherein the controller is adapted to, in response to a user generated signal, construct a filter to cancel noise received at a user-selected time.

16. The headphone of claim 15, wherein the constructed filter is stored in memory, and is activated in response to a user generated signal.

17. The headphone of claim 16, wherein the controller is adapted to, in response to a user generated signal, select noise received at a user-selected time in a band to be in a pass-through band, whereby selected noise within the pass through band is not cancelled.

18. The headphone of claim 11, wherein the microphone comprises first and second microphone, and the detected signal comprises a pattern of pulses received at the first and second microphones.

19. The headphone of claim 11, wherein the detected signal comprises pulses and intervals therebetween, wherein the intervals between pulses exceed a threshold.

* * * * *